(12) United States Patent
Diana et al.

(10) Patent No.: US 10,376,399 B2
(45) Date of Patent: Aug. 13, 2019

(54) IMPLANTABLE DEVICE TO TREAT OBESITY

(71) Applicant: INSTITUT HOSPITALO-UNIVERSITAIRE DE CHIRURGIE MINI-INVASIVE GUIDEE PAR L'IMAGE, Strasbourg (FR)

(72) Inventors: Michele Diana, Vaud (CH); Peter Halvax, Pecs (HU); Fernand Martel, Offlanges (FR); Bruno Mutet, Haguenau (FR); Lee Swanstrom, Portland, OR (US)

(73) Assignee: INSTITUT HOSPITALO-UNIVERSITAIRE DE CHIRURGIE MINI-INVASIVE GUIDEE PAR L'IMAGE, Strasbourg (FR)

( * ) Notice: Subject to any disclaimer, the term of this patent is extended or adjusted under 35 U.S.C. 154(b) by 589 days.

(21) Appl. No.: 15/025,441

(22) PCT Filed: Sep. 29, 2014

(86) PCT No.: PCT/EP2014/070810
§ 371 (c)(1),
(2) Date: Mar. 28, 2016

(87) PCT Pub. No.: WO2015/044422
PCT Pub. Date: Apr. 2, 2015

(65) Prior Publication Data
US 2016/0235569 A1    Aug. 18, 2016

Related U.S. Application Data

(60) Provisional application No. 61/884,058, filed on Sep. 29, 2013.

(51) Int. Cl.
*A61F 5/00* (2006.01)

(52) U.S. Cl.
CPC ............ *A61F 5/0059* (2013.01); *A61F 5/003* (2013.01); *A61F 5/0013* (2013.01);
(Continued)

(58) Field of Classification Search
CPC .... A61F 5/0059; A61F 5/0063; A61F 5/0069; A61F 5/0086
(Continued)

(56) References Cited

U.S. PATENT DOCUMENTS 6,540,789 B1    4/2003  Silverman et al.
6,656,194 B1   12/2003  Gannoe et al.
(Continued)

FOREIGN PATENT DOCUMENTS

DE    10 2012 220 697 A1    5/2014
WO       2009/096857 A1    8/2009
(Continued)

OTHER PUBLICATIONS

International Search Report, dated Jan. 14, 2015, from corresponding PCT Application.

*Primary Examiner* — Samuel G Gilbert
(74) *Attorney, Agent, or Firm* — Young & Thompson

(57) ABSTRACT

An implantable device to treat obesity and a method of using the same, the device (31) is able to create a repetitive mechanical constraint on a gastrointestinal organ wall and includes: an energy source (36), and a mechanical stimulation element (35).

20 Claims, 9 Drawing Sheets

(52) U.S. Cl.
CPC .......... *A61F 5/0063* (2013.01); *A61F 5/0069* (2013.01); *A61F 2005/002* (2013.01)

(58) Field of Classification Search
USPC .......................................................... 600/37
See application file for complete search history.

(56) References Cited

U.S. PATENT DOCUMENTS

| | | | |
|---|---|---|---|
| 8,021,384 | B2 | 9/2011 | Weiss et al. |
| 8,591,396 | B2 * | 11/2013 | Zemlok ................. A61F 5/0059 600/29 |
| 8,942,828 | B1 * | 1/2015 | Schecter .................. A61N 1/05 607/116 |
| 2003/0158564 | A1 | 8/2003 | Benchetrit |
| 2005/0065571 | A1 | 3/2005 | Imran |
| 2005/0245957 | A1 | 11/2005 | Starkebaum et al. |
| 2007/0049986 | A1 | 3/2007 | Imran |
| 2009/0093836 | A1 | 4/2009 | Feld |
| 2012/0022322 | A1 * | 1/2012 | Pasricha ............... A61F 5/0003 600/37 |
| 2012/0116182 | A1 | 5/2012 | Wong et al. |
| 2013/0002095 | A1 | 1/2013 | Van Der Linden |
| 2013/0281911 | A1 | 10/2013 | Babkes et al. |
| 2013/0289466 | A1 | 10/2013 | Babkes et al. |
| 2014/0081419 | A1 | 3/2014 | Silverman et al. |

FOREIGN PATENT DOCUMENTS

| | | |
|---|---|---|
| WO | 2011/130721 A1 | 10/2011 |
| WO | 2014/076458 A1 | 5/2014 |

\* cited by examiner

IMPLANTABLE DEVICE TO TREAT OBESITY

BACKGROUND OF THE INVENTION

Field of the Invention

The present invention relates generally to the fields of surgery and of treatment of medical condition of a mammals subject.

More specifically, the present invention provides an implantable device to treat obesity and a method making use of the same.

Description of the Related Art

Numerous devices, products and methods of various kinds (for example surgical, physical, medicinal) are already known in relation to the treatment of obesity of mammals, making use of different ways to try to achieve a beneficial effect in relation to said medical condition.

Among these known treatment methods, quite a large number make use of implanted or injected devices to achieve the purpose of helping the subject to lose weight.

A first type aims to reduce the inside volume of the stomach, either by compressing or segmenting said organ with a device extending around it, such as a belt or a ring or by locating and possible deploying within the stomach cavity a voluminous or deforming implant in order to reduce the interior empty space and/or to deform the gastric wall (see US 2013/289466 and WO 2011/130721 for example).

An other type aims to limit the ingestion and/or circulation of nutrients by providing a passive or active restriction means inhibiting or slowing down the filling and/or emptying of the stomach (see for example US 2012/116182, US 2003/158564, US 2014/0081419, US 2013/281911).

Now, devices of these two types are an obstacle to the free circulation of ingested food through the gastrointestinal path and adversely affect the smooth functioning of the stomach. They may also create a feeling of discomfort for the implanted subject, and generally request extensive surgery.

A third type of implants, of a passive type, aims to stiffen and/or stretch the stomacal wall by injecting stiffening material or inserting hollow bodies into it (see for example US 2012/022322, US 2014/081419), possibly incorporating a stretching means (US 2009/093836).

Here also extensive surgery is generally needed and no active control is possible.

A fourth type of known devices concerns swallowable devices, such as a device embedded in a capsule, which deploy and/or become active when reaching the stomach. Said devices may stimulate mechanic-receptors by exerting a pressure or vibration action on an organ from within said organ (see for example U.S. Pat. No. 8,021,384).

These latter devices, in addition to being an obstacle to free circulation, cannot be positioned accurately and may be located at the wrong place in terms of obesity treatment efficiency.

Furthermore, due to the deformable nature of the gatrointestinal tract and due to the absence of physical link with its wall, the action points or areas of these devices may change over time, leading to non foreseeable effects.

BRIEF SUMMARY OF THE INVENTION

It is a main purpose of the present invention to propose an alternative solution for treating obesity which is efficient, reliable, long lasting, well tolerated by the subject, non obstructive, independent of the subject's personal implication (automatic functioning) and easily adaptable to specific needs, as well as possibly reprogrammable or resettable during treatment.

Furthermore, the invention should also make use of a device which is of an easily implantable shape and size (preferably using only mini invasive surgery) and of simple structure, can be positioned precisely at an identified locus, is with no discomfort for the subject, is easy and cheap to produce, and possibly easily programmable and controllable without discomforting the implanted subject.

In order to achieve at least the main goals set hereinbefore, the invention concerns according to one of its aspects an implantable device to treat obesity, said device being able to create a repetitive mechanical constraint on a gastrointestinal organ wall and comprising:

An energy source,
A mechanical stimulation means.

The invention is based on the surprising observation made by the inventors that a repetitive mechanical constraint on a gastrointestinal organ wall, for example the stomach wall, creates a feeling of satiety for the subject, allowing to treat obesity by treating its most obvious and frequent cause.

Thus, according to the invention, the said device is adapted to be implanted on the surfaces of and/or within the gastrointestinal wall. Said implantable device is adapted to exert a repetitive mechanical constraint on said gastrointestinal wall. Said mechanical constraint exerted by said implantable device on said gastrointestinal wall of a mammal induces a neurohumoral response creating satiety in said mammal.

Said implantable device may further comprise:
an anchoring means,
a control module capable of activating, deactivating and modulating parameters of said device, preferably programmable and/or
a communication module capable of remotely emitting and receiving information, said information being transferred to and interpreted by said control module.

According to various embodiments of the invention, the mechanical stimulation means may comprise:
at least one piezoelectric element, preferably one element of a plate or stripe like shape,
at least one balloon,
means able to deform a deformable housing lodging said means and forming part of the device.

Preferably, the shape and size of its constitutive components, or at least of some of them, are adapted for affixed mounting on or inserted mounting within the wall of a gastrointestinal organ, preferable the organ to be submitted to repetitive constraint, at a selected implantation site.

In order to have an optimised effect, the invention may provide that the mechanical stimulation means, or at least its part(s) or component(s) providing the repetitive mechanical constraint, has(have) a given surface extension, able to cover a substantial part of the wall, the considered means or component(s) having also a relative stiffness when not activated.

Alternate practical non limitative constructions of the device can be contemplated, wherein for example:
the mechanical stimulation means comprises two balloons connected together through a passage provided with a blowing or circulating module, able to displace a fluid from one balloon to the other, only in one way or in both ways, one of said balloons acting possibly also as an anchoring means,
at least the mechanical stimulation means and preferably also the energy source, the control module and/or the communication module, is (are) installed in a housing, made of a substantially rigid or a deformable material and possibly provided with anchoring means, for example integrally formed with said housing, the mechanical stimulation means comprises one or several arm(s), extending in different directions, located completely within or at least partly outside a housing possibly lodging the energy source and the control and communication modules, said arm(s) being rigid or flexible and put in motion by corresponding actuating means, the anchoring means comprises a base, preferably of a plate or sheet like shape, able to be implanted on or within a organ wall, and provided with an engagement means, preferably integrally formed, for reversibly engaging the mechanical stimulation means, preferably located within a housing.

Several practical embodiments and configurations of the energy source can also be envisaged, wherein for example:

the energy source comprises a mechanical or electrical energy storage means, such as for example a rechargeable battery, and an energy harvesting or producing means, connected to said energy storage means and preferably located outside and possibly separate from the housing, the energy harvesting means consists of a radiofrequency energy collecting means, such as for example an antenna, the energy producing means consists of a means able to convert deformations or movements of at least one organ, in particular of a part of a nearby organ or of the gastrointestinal tract, or a movement of the considered mammal subject, into electrical or mechanical energy.

The produced repetitive mechanical constraint may be more or less extensive, intense and fast consist of a vibration or a cyclic deformation applied to the considered organ wall.

All functional components of the device may be located inside an adapted housing. But it can also be envisaged to propose an implantable device wherein the energy source, the control module and the communication module are located inside a housing, the mechanical stimulation means being located, partly or completely, outside said housing and connected to the energy source.

The invention also encompasses a method to treat obesity comprising the steps of:
identifying a gastrointestinal wall locus,
providing an implantable device, as mentioned before,
implanting said implantable device at said locus,
monitoring and adjusting parameters of said implantable device.

BRIEF DESCRIPTION OF THE DRAWINGS

The invention will be better understood thanks to the following description and drawings of embodiments of said invention given as non limitative examples thereof, wherein in said drawings:

FIG. 8a is a schematic partial view of a part of an implantable device in accordance with yet another embodiment of the present invention;

FIG. 8b is a schematic view of an implantable device in accordance with embodiments of the present invention incorporating the part shown on FIG. 8a;

DETAILED DESCRIPTION OF THE PREFERRED EMBODIMENTS

Figure 1:
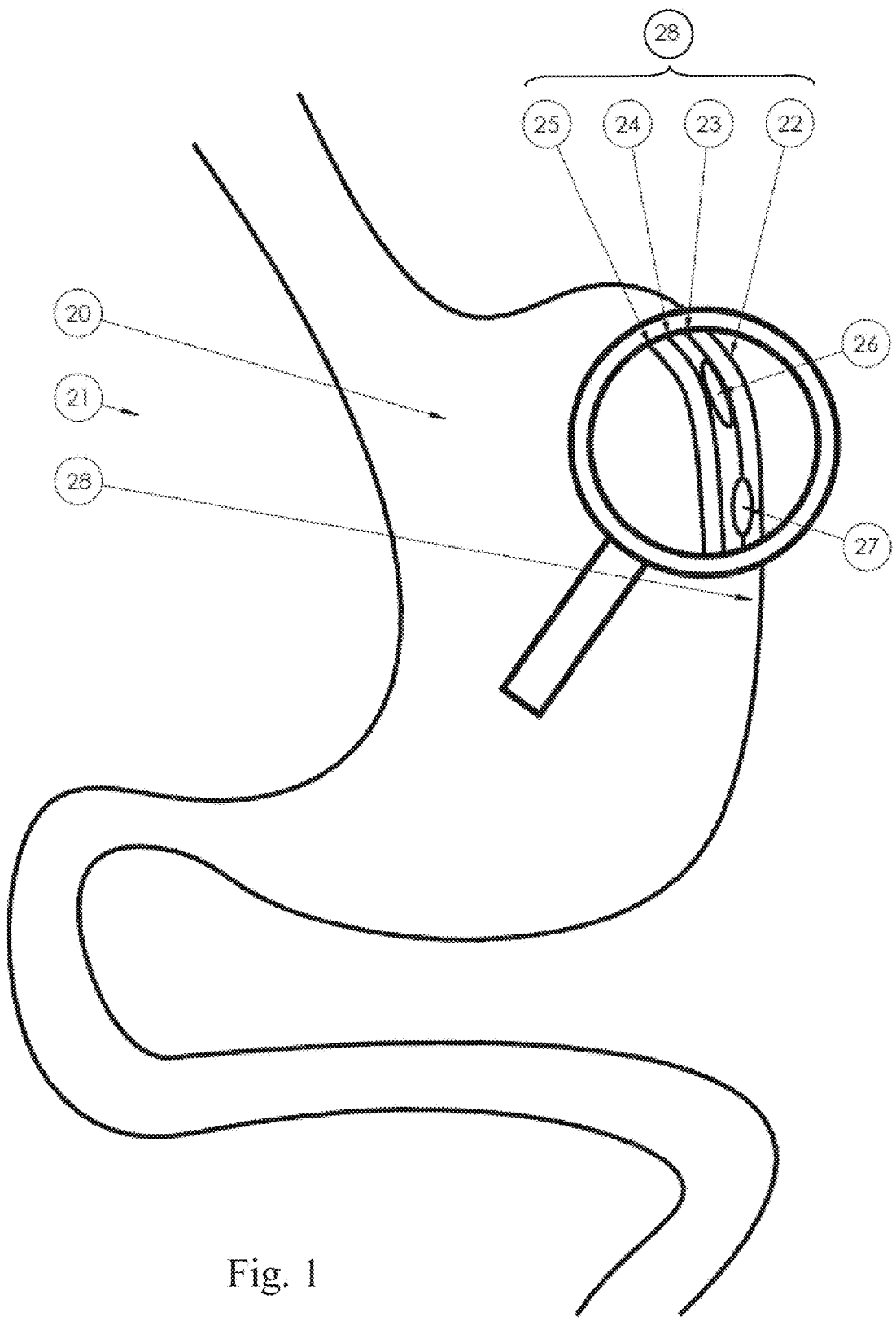
FIG. 1 is a cross sectional view with an enlarged zone of the gastrointestinal tract of a mammal, showing potential spaces able to lodge a device according to the invention.

Referring to FIG. 1, the gastrointestinal tract 21 of a mammal generally defines a lumen 20. Said lumen 20 extension is defined by a wall 28. Said wall 28 comprises various layers. The interior layer is the mucosa 25. Wall 28 further comprises an exterior layer 22 and a muscular layer 23. Muscular layer 23 is placed closer to lumen 20 than the exterior layer 22. The wall 28 further comprises a submucosal layer or submucosa 24 extending between mucosa 25 and muscular layer 23.

A submucosal space 26, that is a potential space, can be created between submucosa 24 and muscular layer 23 by the separation of submucosa 24 from muscular layer 23. In addition, as with any muscle, wall 28 includes an intramuscular space 27, that is a potential space which can be created intramuscularly within the exterior layer 22.

Thus possible loci for the device 31 may comprise the potential internal spaces 26 and 27, as well as the interior face of the mucosa 25 or the exterior face of the exterior layer 22.

Figure 2:
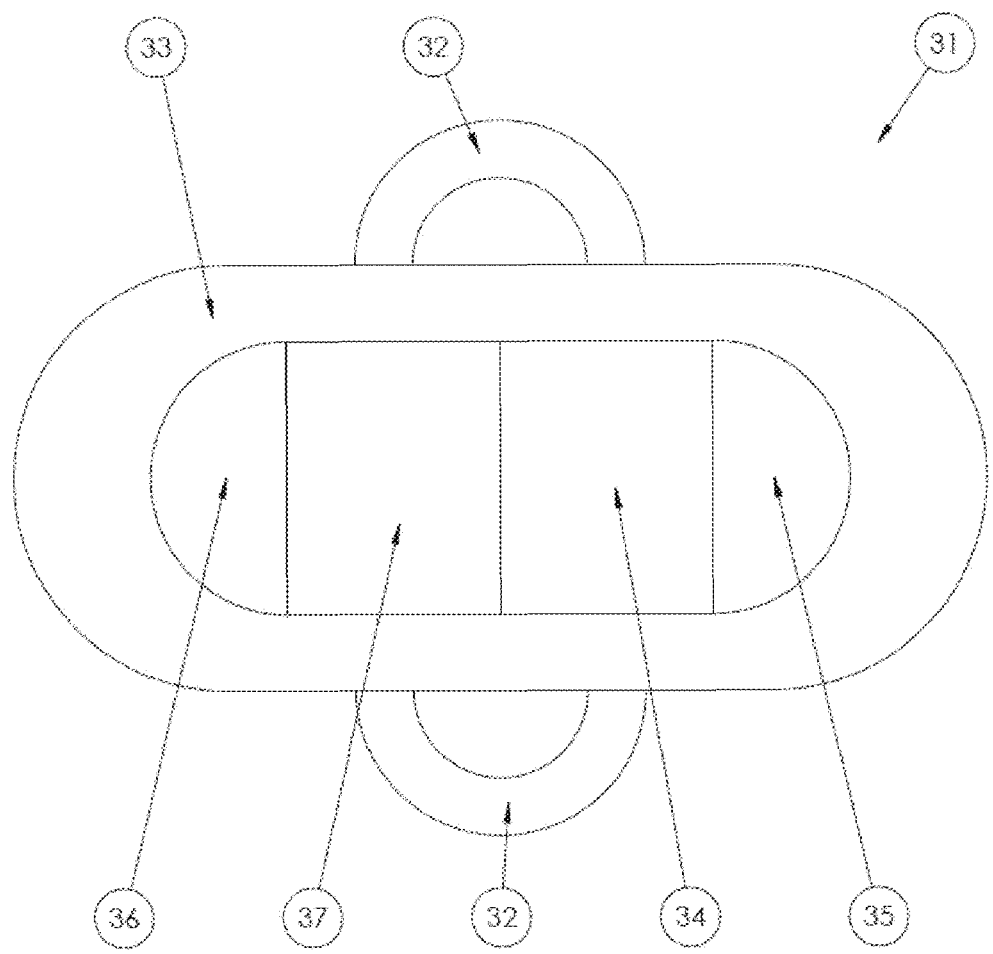
FIG. 2 is a schematic view of an implantable device in accordance with a first embodiment of the present invention.

In a general embodiment of the present invention illustrated for example on FIG. 2, an implantable device 31 comprises a housing 33 and a mechanical stimulation means 35. Said implantable device 31 is intended to be implanted at least in contact with a wall 28 and to provide a mechanical constraint to the wall 28 through the action of said mechanical stimulation means 35.

In some embodiments of the present invention, implantable device 31 may comprise an anchoring means 32, said anchoring means 32 allowing the implantable device 31 to be coupled to wall 28 and allowing housing 33 and or mechanical stimulation means 35 to be at least partially in contact with a wall 28. Said anchoring means 32 may for example be, but is not limited to, a means (for example an eyelet) enabling suturing an implantable device 31 to the wall 28 or polymerizable glue. Examples of these two anchoring solutions are known in the state of the art.

According to the present invention, the implantable device 31 comprises an energy source 36. Said energy source 36 may provide electrical or mechanical energy. Said energy source 36 may for example be, but is not limited to, a battery, radio-frequency energy transmission or a system harvesting energy from the body in the vicinity of the implantation site of implantable device 31. Such energy harvesting systems include, but are not limited to, piezo-electric element harvesting energy from deformations and constraints or weight systems such as those known for automatic watches. Energy harvesting elements can be used in conjunction with a battery so that the device can be actuated even when the conditions for energy production are not met.

In some embodiments of the present invention, an implantable device 31 is adapted to be implanted on the surface of the exterior layer 22 or on the surface of the mucosa 25 and or within the submucosal space 24 or intramuscular space 27 of the wall 28 of a gastrointestinal tract 21.

In one embodiment, an implantable device 31 is implanted on the surface or within the wall 28 of a gastro-intestinal tract 21 in the vicinity of or in contact with vessels thus providing a mechanical constraint to said vessels. Such vessel stimulation has an effect on satiety.

In some embodiments of the present invention, an implantable device 31 comprises a communication module 37, enabling information to be remotely exchanged between said implantable device 31 and another communication unit located outside the subject, preferably in its close vicinity. Said communication unit, can for example be, but is not limited to, a computer, a tablet or a cellular phone. Such communication module 37 using for example Radio Frequency waves, for exchanging information, and possibly transmitting energy to, the implanted device 31, are known in the art.

In some embodiments of the present invention, an implantable device 31 normally comprises a control module 34. Said control module 34 is able to activate and deactivate said mechanical stimulation means 35 and to manage operation of mechanical stimulation means 35. Said control module 34 can further be pre-programmed to control mechanical stimulation means 35 according to an operation sequence. Parameters of said mechanical constraints can be changed by control module 34. Said parameters include but are not limited to duration, strength, amplitude, frequency, time of activation and deactivation of said mechanical stimulation means 35.

In some embodiments, control module 34 may comprise sensors (not shown) able to measure various parameters of the implantable device 31 status, such as temperature, battery charge level, mechanical stimulation means 35 status or any other parameter.

In some embodiments of the present invention, the implantable device 31 may comprise a communication module 37 and a control module 34. Implantable device 31 is then adapted such that information received by said communication module 37 can be transmitted to control module 34 and interpreted by control module 34 and such that information gathered by control module 34 can be transmitted to communication module 37. Such a technical solution is known in the art. Said parameters of said mechanical constraints applied to wall 28 by mechanical stimulation means 35 can thus be changed remotely and the status parameters of implantable device 31 can be monitored remotely.

In the embodiment shown on FIG. 2, an implantable device 31 comprises a housing 33, a mechanical stimulation means 35, a communication module 37, an energy source 36 and a control module 34.

In this embodiment the mechanical stimulation means 35 is enclosed inside the housing 33. The mechanical stimulation means 35 can be, but is not limited to, a vibrating means. Said vibrating means can be for example an eccentric rotating mass vibration motor or a piezoelectric element.

Figure 3:
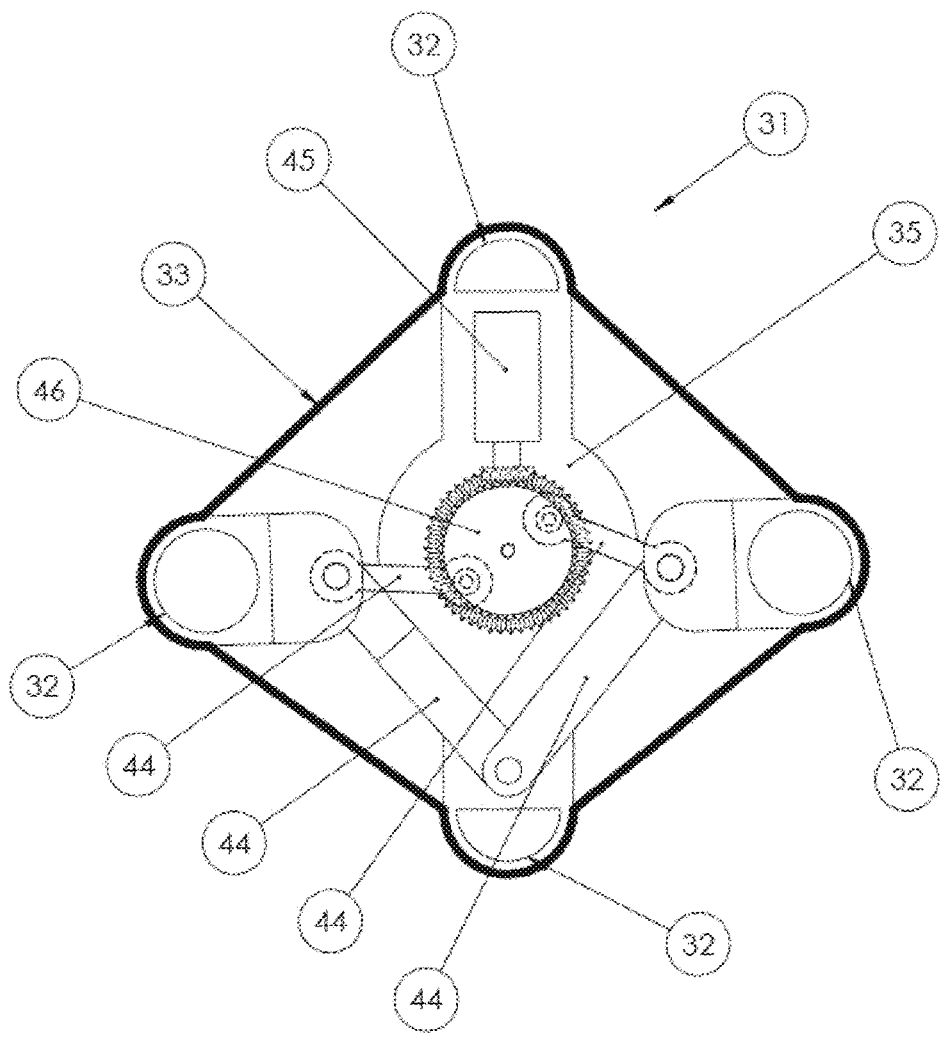
FIG. 3 is a cross sectional view of an implantable device in accordance with another embodiment of the present invention.

In an alternative embodiment, and as shown on FIG. 3, the housing 33 may be made from a deformable material. Mechanical stimulation means 35 comprises for example a motor 45, a mechanical intermediary mechanism 46 and a plurality of arms 44. Motor 45 is dynamically coupled to mechanical intermediary mechanism 46. Mechanical intermediary mechanism is coupled to at least one arm 44. Each arm 44 is dynamically coupled to two other arms 44 in a manner allowing all arms 44 to be set to motion when mechanical intermediary mechanism 46 is set to motion.

When implantable device 31 is actuated the housing 33 continuously deforms under the action of the mechanical stimulation means 35 providing a mechanical constraint on the wall 28.

In another embodiment, the mechanical stimulation means 35 can be a part of the housing 33. In this embodiment the vibrating surface of the piezoelectric element is coplanar with the housing 33, such that said vibrating surface of the piezoelectric element can be put in direct contact with wall 28.

In some other embodiments of the present invention, illustrated on FIG. 4, the mechanical stimulation means 35 may extend partly outwardly from housing 33.

Figure 4A:
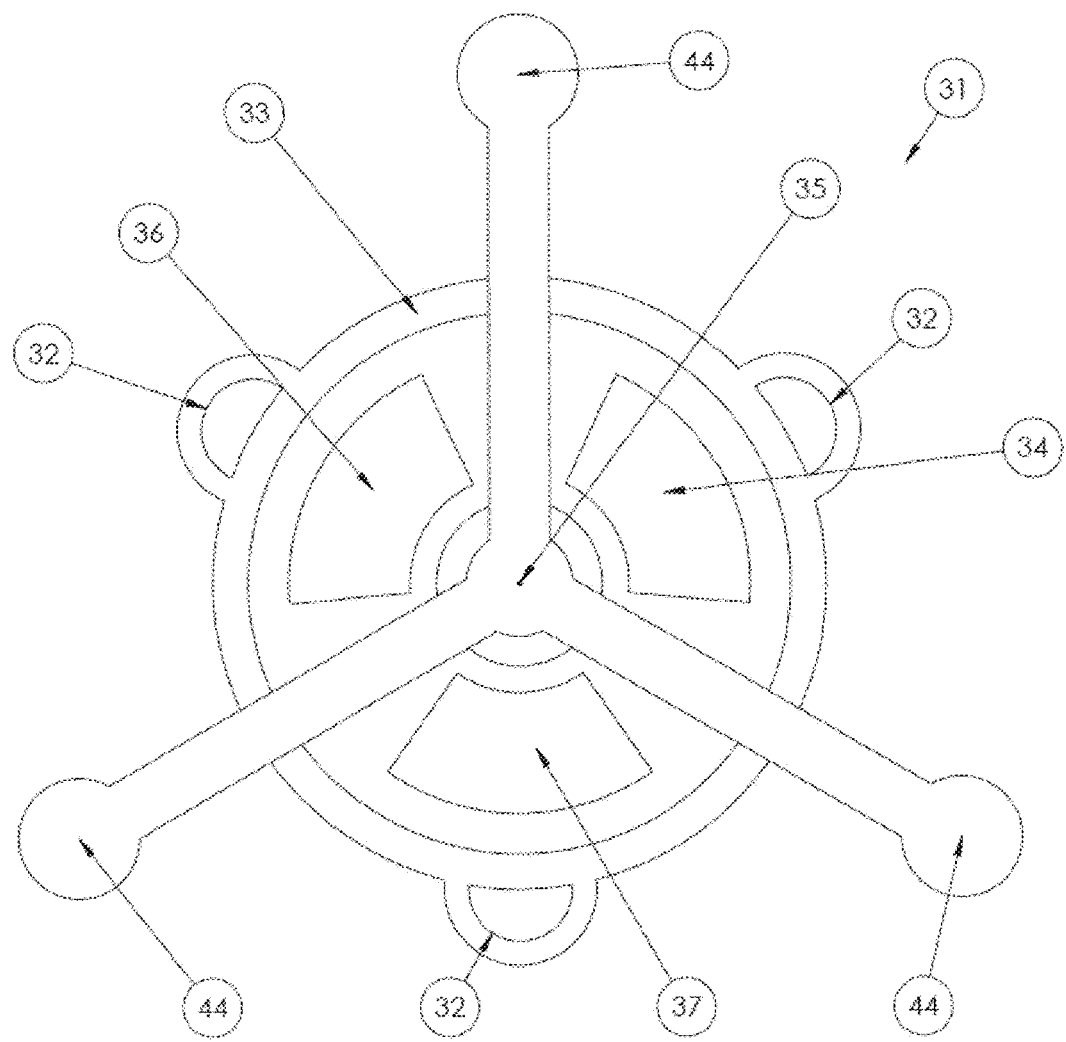
FIG. 4a is a schematic view of an implantable device in accordance with yet another embodiment of the present invention.

In another embodiment, shown in FIG. 4a, mechanical stimulation means 35 comprises at least one arm 44 extending outwardly from the housing 33. Said mechanical stimulation means 35 further comprises a motor. Said motor is coupled to said arm 44. Said arm 44 can be set to motion by said motor. The implantable device 31 further comprises anchoring means, allowing said arm 44 to be at least partially in contact with a wall 28.

Figure 4B:
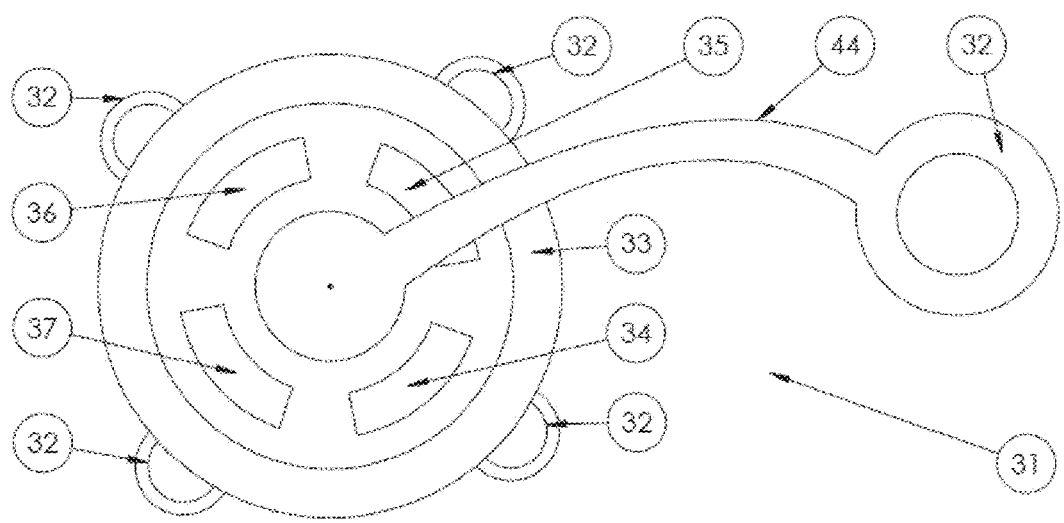
FIG. 4b is a schematic view of an implantable device in accordance with yet another embodiment of the present invention.

In another embodiment, shown on FIG. 4b, the distal part of said arm 44 comprises an anchoring means 32 allowing the distal part of said arm 44 to be attached to the wall 28. Said arm 44 may further be made of a deformable or bendable material such that mechanical constraints are provided to wall 28 through the contact with the whole length of the arm 44.

Figure 5A:
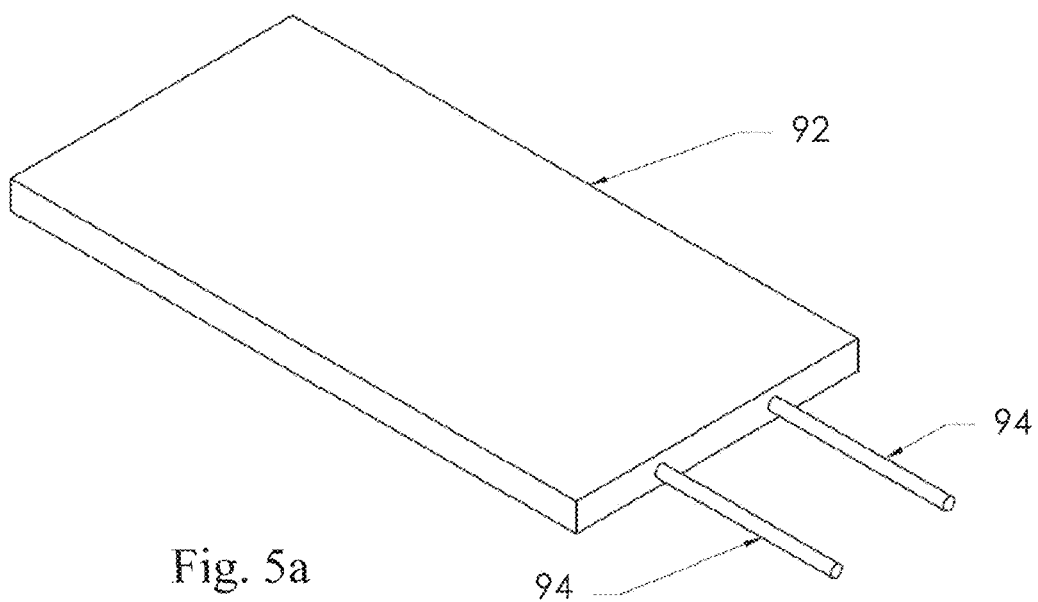
FIGS. 5a and 5b are perspective view of a piezoelectric plate respectively in flat and bended configurations.
Figure 5B:
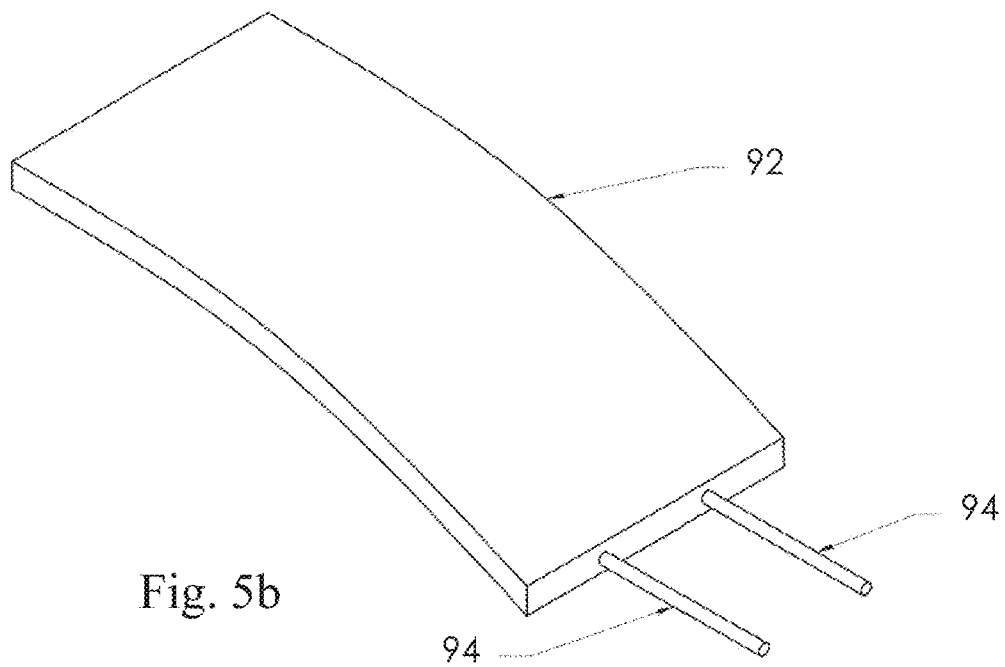
Figure 6:
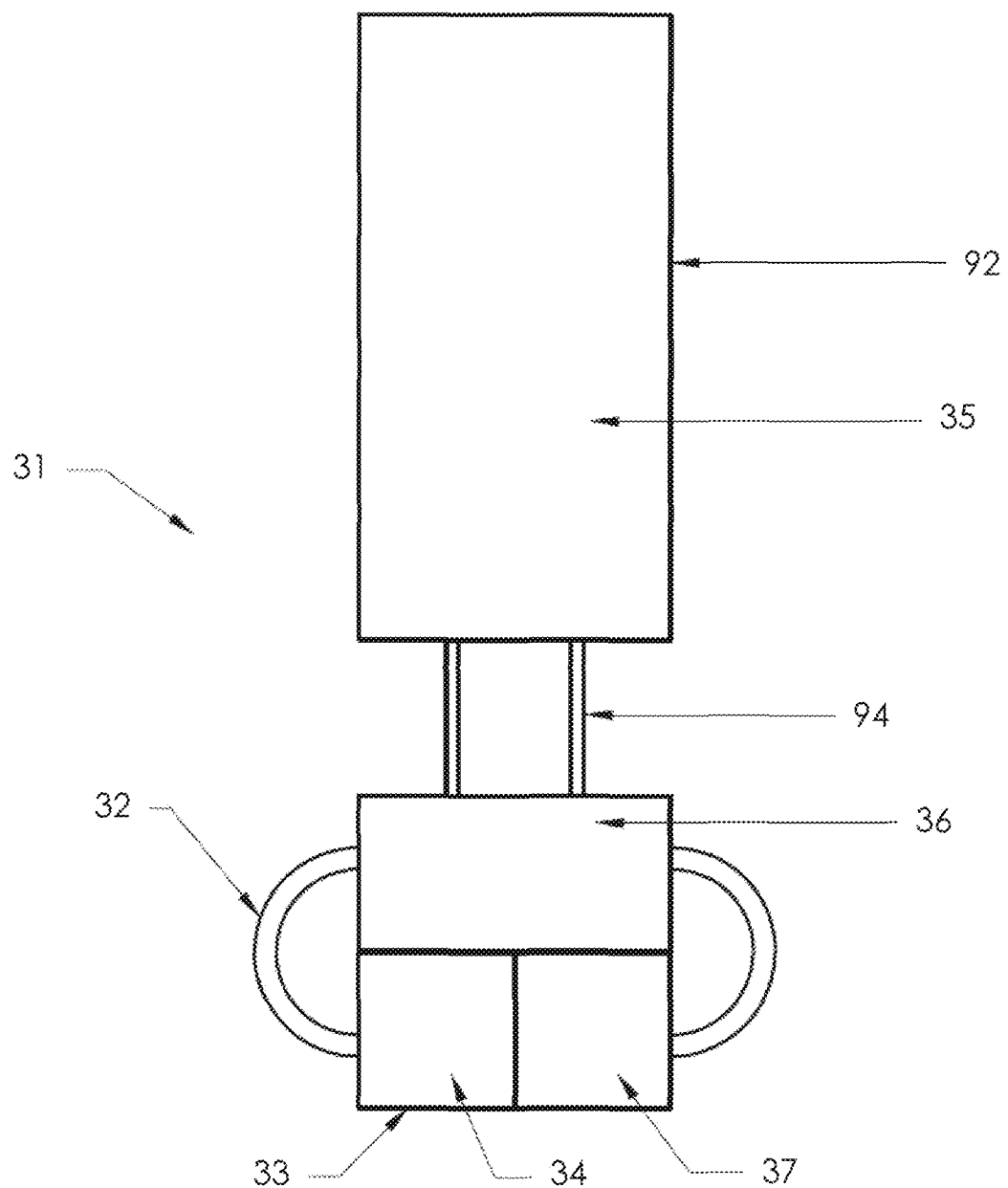
FIG. 6 is a schematic of an implantable device in accordance with yet other embodiments of the present invention.

In a general alternate embodiment, the stimulation means 35 is located outside the housing 33. FIGS. 5a, 5b and 6 illustrate such embodiments.

In one embodiment, the mechanical stimulation means 35 is a piezoelectric plate 92. Said piezoelectric plate 92 is substantially planar. When supplied with electric current, said piezoelectric plate 92 bends and adopts a curved profile as shown in FIG. 5b. Under an appropriate electrical power supply, said piezoelectric plate 92 can oscillate between flat and bended configurations. Such piezoelectric plates are known in the art such as the one disclosed by publication US 2013002095 (whose content is entirely integrated herein by reference). The piezoelectric plate 92 is connected to the energy source 36 by means of insulated electrical connectors 94.

When said piezoelectric plate 92 is used as the mechanical stimulation means, the stimulation provided by the implantable device 31 covers an area as large as the surface of the piezoelectric plate. Said area of stimulation can be adapted by adapting the dimensions and/or shape of the piezoelectric plate 92. Given the shape and the resilience of said piezoelectric plate 92, when implanted, the implantable device 31 has a stiffening effect on a gastrointestinal wall, thus creating a satiety inducing effect.

In one embodiment, an array of or multiple piezoelectric plates can be used to target multiple sites within a gastrointestinal wall and to increase the wall stiffening effect.

Another type of piezoelectric element, preferably also in the shape of a plate can be adapted to convert a deformation into electrical current. This element thus acts as an energy generating or harvesting piezoelectric plate. Harvesting piezoelectric plates are known in the art and are described for example in the disclosure of DE 102012220697.

In one embodiment, the implantable device 31 comprises harvesting piezoelectric plates 92 as energy producing or harvesting modules. When the implantable device 31 is implanted on the surface of or within a wall 28 of the gastrointestinal tract, the piezoelectric harvesting plates are deformed by the natural movements of the organs and thus produce electrical energy. The energy produced can be stored in a battery. The energy stored can then be used to actuate the implantable device 31.

Piezoelectric harvesting plates also have a stiffening effect on the wall where they are implanted. This stiffening effect has itself a satiety inducing effect. A plurality of piezoelectric harvesting plates can be used simultaneously to increase the amount of energy harvested and the stiffening effect.

Figures 7A, 7B:
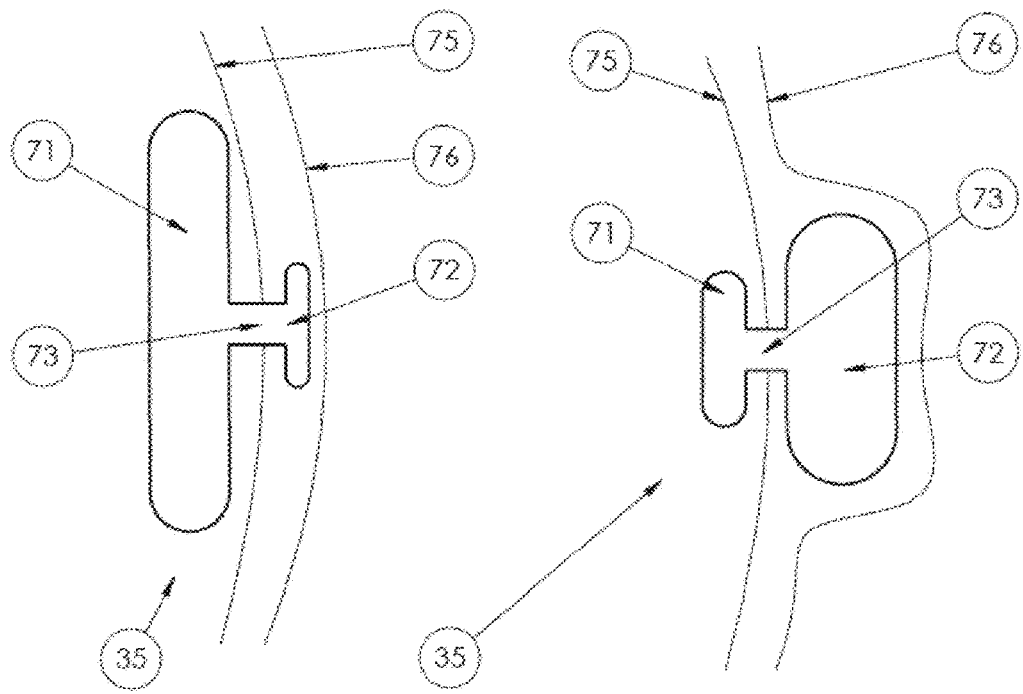
FIG. 7a and FIG. 7b are schematic views of an implantable device in accordance with yet another embodiment of the present invention, the device being in two different states.

In another embodiment, shown in FIGS. 7a and 7b, mechanical stimulation means 35 comprises at least a first balloon 71 and a second balloon 72 (both made of an elastically deformable material) and a blowing or circulating module 73, known to a man skilled in the art, allowing to periodically empty said first balloon 71 from a fluid and fill said second balloon 72 with said fluid. The second balloon 72 can be placed in a submucosal space 26 or intramuscular space 27. The blowing or circulating module 73 is located within or around a communicating passage connecting the two balloons.

The two balloons may have different shapes. An elongated shape is preferred for the second balloon 72 as it implies a wall 28 rigidification action amplifying the satiety inducement effect.

In one embodiment, said blowing module 73 allows to periodically empty said second balloon 72 from a fluid and fill said first balloon 71 with said fluid.

In an alternative embodiment said second balloon 72 can be emptied (and the first balloon filled) by natural movements of the wall 28.

The blowing or circulating module 73, such as for example a micro pump, will of course be provided with energy and control signals by the corresponding means 34 and 36 lodged within a housing 33, the latter being located remotely from, next to or within one of the balloons 71, 72.

Figures 8A, 8B:
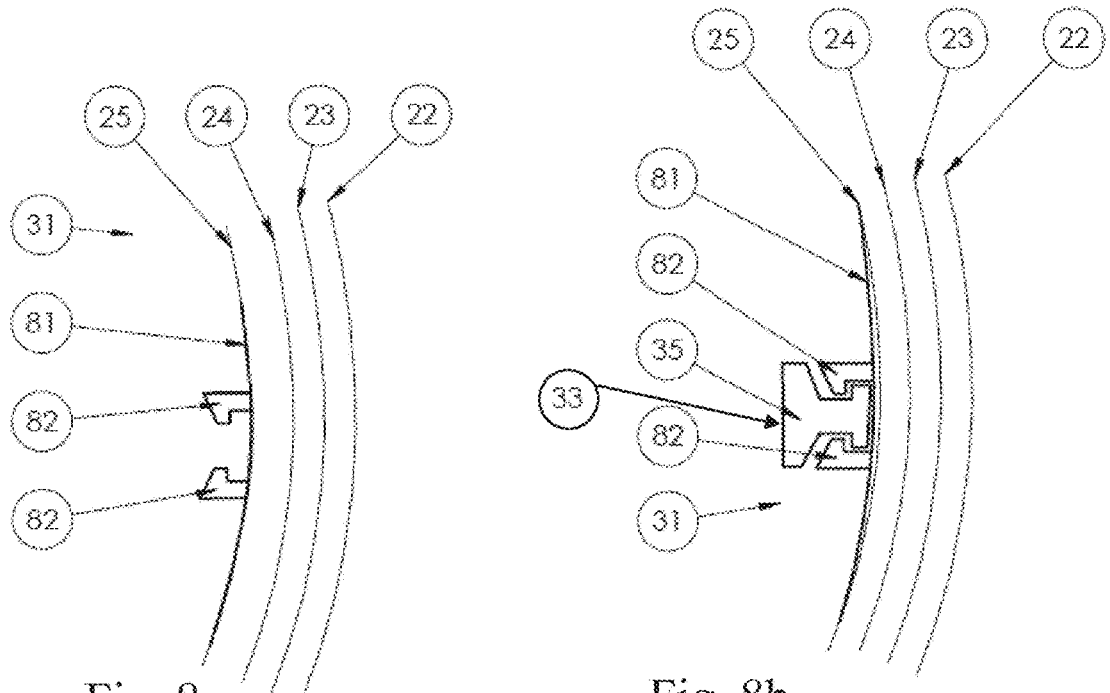

In another embodiment shown on FIG. 8a, the implantable device 31 comprises a base 81. When implantable device 31 is implanted on and or within a wall 28, said base enables a large contact surface with said wall 28. Said base 81 includes an anchoring means, not visible on FIGS. 8, allowing the base 81 to be coupled to said wall 28. Said base 81 further includes an engagement means 82 to reversibly engage housing 33.

In a preferred embodiment shown on FIG. 8b, the mechanical stimulation means 35 is enclosed within the housing 33 and base 81 is engaged to wall 28 using a polymerizable glue as an anchoring means. In such an embodiment, implantable device 31 provides a wall 28 rigidification action increasing satiety feel in a mammal in which implantable device 31 has been implanted.

The sheet or plate like base 81 can be linked intimately to the wall 28 locally or continuously over all its surface. Said base 81 forms with said engagement means 82 a mounting interface for the mechanical stimulation means 35, also able to transmit the constraint to the wall.

By just implanting one or several devices 31 having a surface covering shape on or in the organ wall 28, a stiffening of said wall is achieved which, even in the absence of positive or active constraint, provides already a noticeable satiety feeling.

The man skilled in the art understands that the or each device 31 may comprise several mechanical stimulation means 35, possibly of different kinds, and several energy harvesting means and/or energy sources, possibly of different kinds.

When several devices 31 are implanted, their respective actions may be globally coordinated.

It is also an object of the present invention to provide a method to treat obesity.

Figure 9:
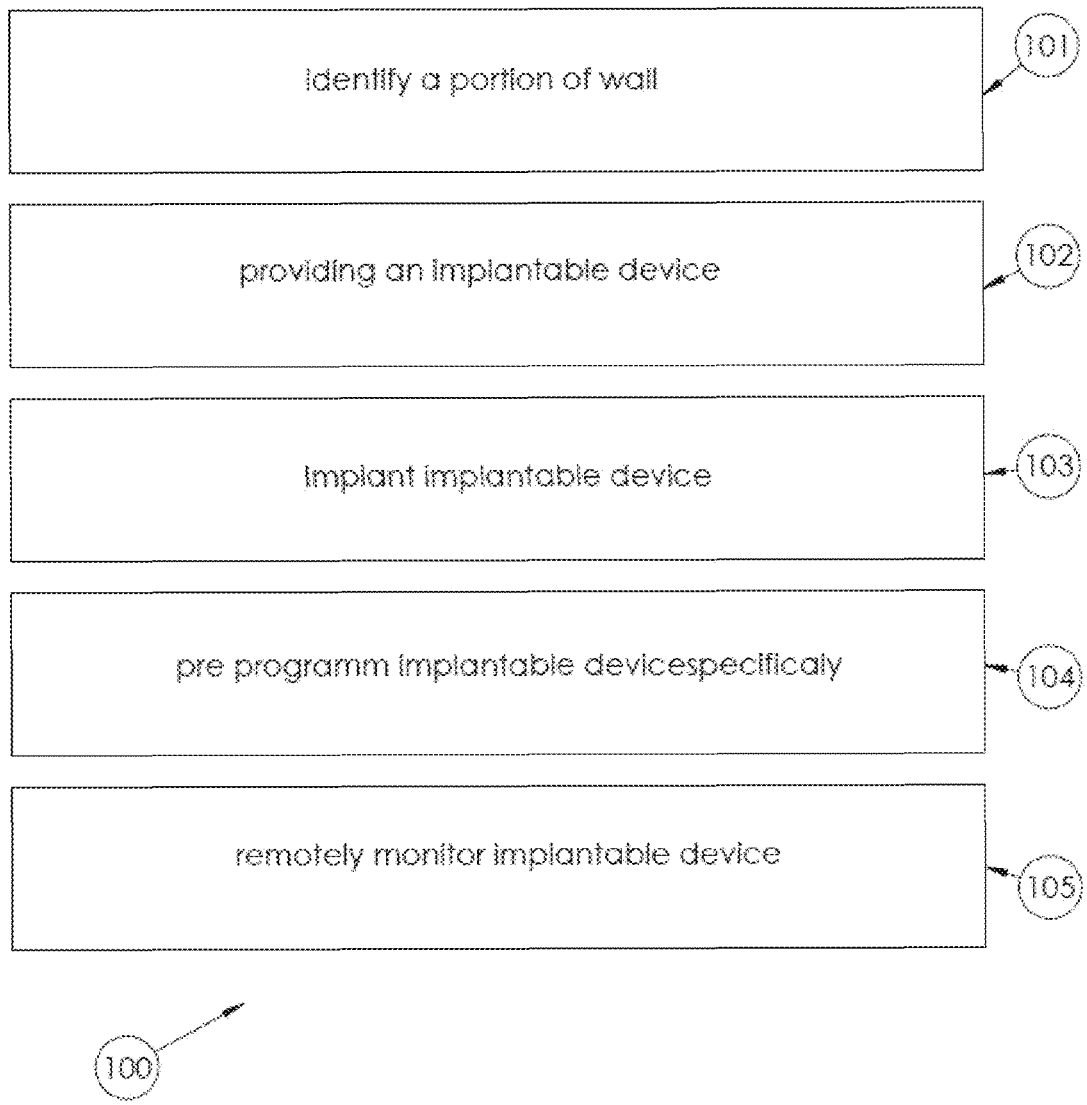
FIG. 9 is a representation of the main steps of a method to treat obesity in agreement with the present invention.

Referring to FIG. 9, such a method to treat obesity generally comprises the following steps: identifying a portion of wall 28 sensitive to mechanical constraint, providing an implantable device 31, implanting said implantable device 31 on one of the surfaces of or within said portion of wall 28.

In another embodiment, a method to treat obesity further comprises the step of remotely monitoring said implantable device 31 to adjust mechanical stimulation parameters.

In another embodiment, the step of implanting said implantable device 31 on one of the surfaces of or within said portion of wall 28 is done using minimally invasive techniques.

In another embodiment, the implantable device 31 is pre-programmed specifically for the mammal to be treated before implantation.

The present invention is, of course, not limited to the preferred embodiments described and represented herein, changes can be made or equivalents used without departing from the scope of the invention.

The invention claimed is:

1. An implantable device to treat obesity, said device (31) being able to create a mechanical constraint on a gastrointestinal organ wall and comprising:
   an energy source (36, 92), and
   a mechanical stimulation means (35),
   wherein, upon activation, the mechanical stimulation means (35) undergoes cyclic deformation,
   wherein the mechanical stimulation means (35) is implantable within a wall (28) of a gastrointestinal organ at an implantation site,
   wherein the mechanical stimulation means (35) has a surface extension that, with the mechanical stimulation means (35) adaptable within the wall (28) at the implantation site, adaptable to cover a part of the wall (28) of the gastrointestinal organ at the implantation site,
   wherein, when the mechanical stimulation means (35) is not activated, the surface extension of the mechanical stimulation means (35) has a stiffness that is adapted to provide rigidity to the part of the wall adapted to be covered by the surface extension at an implantation site, and
   wherein the cyclic deformation of the mechanical stimulation means (35) creates a repetitive mechanical constraint on the part of the wall (28) adapted to be covered by the surface extension at the implantation site.

2. The device according to claim 1, further comprising an anchoring means (32).

3. The device according to claim 2, wherein the anchoring means (32) comprises a base (81) able to be implanted within the wall (28) of the gastrointestinal organ, and provided with an engagement means (82) for reversibly engaging the mechanical stimulation means (35).

4. The device according to claim 1, further comprising a control module (34) capable of activating, deactivating and modulating parameters of said device.

5. The device according to claim 4, further comprising a communication module (37) capable of remotely emitting and receiving information, said information being transferred to and interpreted by said control module.

6. The device according to claim 5, wherein the energy source (36), the control module (34) and the communication module (37) are located inside a housing (33), the mechanical stimulation means (35) being located, partly or completely, outside said housing (33) and connected to the energy source (36).

7. An implantable device to treat obesity, said device (31) being able to create a mechanical constraint on a gastrointestinal organ wall and comprising:
an energy source (36, 92); and
a mechanical stimulation means (35),
wherein the device (31) is adapted to create a repetitive mechanical constraint by cyclic deformation of the mechanical stimulation means (35),
wherein a shape and a size of constitutive components of said device (31) are adapted for inserted mounting within a wall (28) of a gastrointestinal organ,
wherein at least a part of the mechanical stimulation means (35) has a surface extension, able to cover a substantial part of the wall (28), the part of the mechanical stimulation means (35) having the surface extension also having a relative stiffness when not activated, and
wherein the mechanical stimulation means (35) comprises at least one piezoelectric element (92).

8. The device according to claim 1, wherein the mechanical stimulation means (35) comprise at least one balloon (71, 72) that is implantable within the wall (28) of the gastrointestinal organ at the implantation site, and
wherein upon the activation of the mechanical stimulation means (35), the at least one balloon (71, 72) undergoes cyclic deformation that creates the repetitive mechanical constraint on the part of the wall (28) adapted to be covered by the surface extension at the implantation site.

9. An implantable device to treat obesity, said device (31) being able to create a mechanical constraint on a gastrointestinal organ wall and comprising:
an energy source (36, 92); and
a mechanical stimulation means (35),
wherein the device (31) is adapted to create a repetitive mechanical constraint by cyclic deformation of the mechanical stimulation means (35),
wherein a shape and a size of constitutive components of said device (31) are adapted for inserted mounting within a wall (28) of a gastrointestinal organ,
wherein at least a part of the mechanical stimulation means (35) has a surface extension, able to cover a substantial part of the wall (28), the part of the mechanical stimulation means (35) having the surface extension also having a relative stiffness when not activated, and
wherein the mechanical stimulation means (35) comprises two balloons (71 and 72) connected together through a passage provided with a blowing or circulating module (73), able to displace a fluid from one balloon to the other, only in one way or in both ways.

10. The device according to claim 1, wherein the mechanical stimulation means (35) comprise deforming means (44, 45, 46) able to deform a deformable housing (35) lodging said means and forming part of the device (31).

11. The device according to claim 1, wherein constitutive components of device (31) are adapted for inserted mounting within the wall (28) of the organ to be submitted to constraint, at the implantation site, in an internal space of said wall (28) chosen among a submucosal space (26) and an intramuscular space (27).

12. The device according to claim 5, wherein at least the mechanical stimulation means (35) and the energy source (36), the control module (34) and/or the communication module (37), are installed in a housing (35), made of a rigid or a deformable material and provided with anchoring means (32).

13. The device according to claim 12, wherein the mechanical stimulation means (35) comprises arms (44) that extend in different directions with respect to each other, the arms located at least partly outside the housing (33) lodging the energy source (36) and the control and communication modules (34, 37), said arms (44) being put in motion by corresponding actuating means (45, 46).

14. The device according to claim 10, wherein the energy source (36, 92) comprises a mechanical or electrical energy storage means (36) and an energy harvesting or producing means (92), connected to said energy storage means (36) and located outside and separate from the housing (35).

15. The device according to claim 14, wherein the energy harvesting means comprises a radiofrequency energy collecting means.

16. The device according to claim 14, wherein the energy producing means (92) comprises a means able to convert deformations or movements of at least one organ, in particular of a part of a nearby organ or of the gastrointestinal tract (21), or a movement of the considered mammal subject, into electrical or mechanical energy.

17. A method to treat obesity, in particular for a mammal subject, comprising the steps of:
identifying a gastrointestinal wall locus (25, 26, 27), sensitive to mechanical constraint,
providing the implantable device (31) of claim 1,
implanting said implantable device at said locus, and
monitoring and adjusting parameters of said implantable device.

18. The method of claim 17, wherein the step of monitoring and adjusting parameters of said implantable device is done remote from the implantable device.

19. The method of claim 17, wherein at least anchoring means (32, 81, 72) of the implantable device are implanted within the gastrointestinal wall (28).

20. The method of claim 17, wherein the device (31), through a housing (33) thereof and/or anchoring means (32, 81) of the implantable device is intimately secured to the gastrointestinal wall (28) on top of the mucosa (25).

* * * * *